(12) United States Patent
Dal Farra et al.

(10) Patent No.: US 8,440,789 B2
(45) Date of Patent: May 14, 2013

(54) PHARMACEUTICAL AND/OR COSMETIC COMPOSITION CONTAINING AN ACTIVE ANTIOXYDANT PRINCIPLE AND CELL ENERGY ACTIVATOR

(75) Inventors: Claude Dal Farra, Opio (FR); Nouha Domloge, Valbonne (FR); Jean-Marie Botto, Valbonne (FR)

(73) Assignee: Societe d'Extraction des Principes Actifs (Vincience), Biot (FR)

( * ) Notice: Subject to any disclaimer, the term of this patent is extended or adjusted under 35 U.S.C. 154(b) by 748 days.

(21) Appl. No.: 12/597,862

(22) PCT Filed: Apr. 23, 2008

(86) PCT No.: PCT/FR2008/000575
§ 371 (c)(1),
(2), (4) Date: Oct. 27, 2009

(87) PCT Pub. No.: WO2008/145852
PCT Pub. Date: Dec. 4, 2008

(65) Prior Publication Data
US 2010/0184637 A1    Jul. 22, 2010

(30) Foreign Application Priority Data

Apr. 27, 2007 (FR) .................................. 07 03063

(51) Int. Cl.
*A61K 38/00* (2006.01)
*A61K 38/04* (2006.01)
*A61K 8/18* (2006.01)

(52) U.S. Cl.
USPC ........... 530/300; 424/59; 514/18.6; 514/18.7; 530/329; 530/330

(58) Field of Classification Search ........................ None
See application file for complete search history.

(56) References Cited

U.S. PATENT DOCUMENTS

| | | | |
|---|---|---|---|
| 6,410,827 B1 | 6/2002 | Cahoon et al. | |
| 7,894,996 B2 * | 2/2011 | Rice et al. ........................ | 702/19 |
| 2006/0013794 A1 | 1/2006 | Dal Farra et al. | |
| 2008/0227725 A1 | 9/2008 | Dal Farra et al. | |

FOREIGN PATENT DOCUMENTS

| | | | |
|---|---|---|---|
| WO | 02/079430 A | 10/2002 | |
| WO | 03/077936 A | 9/2003 | |
| WO | 2004/043482 A | 5/2004 | |
| WO | 2005/097060 A | 10/2005 | |
| WO | WO 2006/090385 | * | 8/2006 |

OTHER PUBLICATIONS

Sherwin, E.R.; "Antioxidants for Vegetable Oils"; J. Am. Oil Chemists' Soc., Jun. 1976 (vol. 53), pp. 430-436.*
Bauza E et al., "A New Peptide That Displays an Uncoupling-Like Effect on the Mitochondrial Respiration Process of Adipocytes and Reduces Adipocyte Lipid Synthesis", Journal of Investigative Dermatology, Mar. 2004, p. A71, vol. 122, No. 3, New York, NY, US, XP009078779.
Gondran C et al., "A new synthetic peptide that exhibits interesting anti-aging effects", Journal of Investigative Dermatology, Apr. 2006, p. 27, vol. 126, No. Suppl. 1, XP009093186 & 67th Annual Meeting of the Society for Investigative-Dermatology, May 3-6, 2006, Philadelphia, PA, USA.
Del Farra et al., "Anti-aging effects observed in new synthetic peptide" J Am Acad Dermatol, Feb. 2007, p. AB25, XP002460912.
Del Farra et al., "An anti-aging effect on the lips and skin observed in in vivo studies on a new fibronectin-like peptide", J Am Acad Dermatol, Feb. 2007, p. AB88, XP002460913.
International Search Report in Corresponding Application No. PCT/FR2008/000575 Dated Nov. 7, 2008.

* cited by examiner

*Primary Examiner* — Robert A Wax
*Assistant Examiner* — Jeffrey T Palenik
(74) *Attorney, Agent, or Firm* — Young & Thompson

(57) ABSTRACT

A cosmetic or pharmaceutical composition, and particularly dermatological composition, comprising, in a physiologically adapted medium, as active principle, polypeptides or peptides, and methods of administering a composition capable of increasing cell energy and to protect the skin from oxidative damage. Also, a cosmetic treatment procedure aimed at protecting the skin and the skin appendages from external aggressions and to combat skin aging.

21 Claims, No Drawings

SEQUENCE LISTING

<160> NUMBER OF SEQ ID NOS: 4

<210> SEQ ID NO 1
<211> LENGTH: 6
<212> TYPE: PRT
<213> ORGANISM: Artificial Sequence
<220> FEATURE:

```
-continued

<223> OTHER INFORMATION: Synthetic Peptide
<220> FEATURE:
<221> NAME/KEY: MOD_RES
<222> LOCATION: (6)..(6)
<223> OTHER INFORMATION: AMIDATION

<400> SEQUENCE: 1

Ala Val Leu Ala Gly Asp
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 2

Ala Val Leu Ala Gly Asp
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 3

Ala Val Leu Ala Gly
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (5)..(5)
<223> OTHER INFORMATION: AMIDATION

<400> SEQUENCE: 4

Ala Val Leu Ala Gly
1               5
```

PHARMACEUTICAL AND/OR COSMETIC COMPOSITION CONTAINING AN ACTIVE ANTIOXYDANT PRINCIPLE AND CELL ENERGY ACTIVATOR

The present invention is in the cosmetic and pharmaceutical field, and more specifically in the field of dermatology. The present invention concerns a cosmetic or pharmaceutical composition, and particularly dermatological, comprising, in a physiologically adapted medium, as active principle, peptides, used alone or in association with at least one other active principle. The invention also relates to the use of a composition capable of increasing cell energy and to protect the skin from oxidative damage. The invention also relates to a cosmetic treatment procedure aimed to protect the skin and skin appendages from external aggressions and to combat skin aging. The active principle can also be used to prepare pharmaceutical compositions aimed at preventing or combating pathologies linked to oxidation processes or also, certain aging pathologies.

According to the invention, the term "skin appendages" includes all keratin annexes present on the surface of the body, in particular the hair, the lashes, the eyebrows, the nails and hair.

The skin is a vital organ which covers the entire surface of the body and insures the protective, sensitive, immune, metabolic or also thermoregulation functions. The skin, like the other organs, is subject to aging. Now, one of the major mechanisms involved in aging processes is the accumulation of oxidative damage in essential molecules such as membrane lipids, proteins, ADN and quite particularly mitochondrial ADN (ADNmt).

Oxidative damage is caused by free radicals, chemically instable and highly reactive molecules, generated by intracellular metabolism or external aggressions. External aggressions include: UV rays, toxins, atmospheric pollutants, food oxidants. In the skin, one observes premature aging manifested in those areas exposed to rays, characterized by macromolecule alteration phenomena (lipid peroxydation, carbonylation of proteins) affecting in particular elastin, collagen or fibronectine. One has also been able to show/demonstrate a progressive decline in the mitochondrial functions with age, probably linked to the accumulation of mutations to ADNmt (K. Singh, Ann. N.Y. Acad. Sci. 1019, 2004).

One of the most important consequences of the accumulation of oxidative damage is a reduction of the cell's capacity to produce ATP (Porteous et al., Eur J Biochem 1998, 257(1): 192-201). Thus, the phenomenon of cellular aging concerns the oxidative damage which the cell suffers/undergoes but also with the energy production processes needed for the cell necessary to survive.

The body possesses defense mechanisms capable of trapping or transforming free radicals (enzymes, glutathione, vitamins A and E, coenzyme Q10, etc.). However, these antioxidant defense systems are often insufficient against the many stress and external aggressions to which the organisms and skin in particular are subjected.

In this context, the antioxidant properties of the coenzyme Q10 appear to be particularly interesting:

Coenzyme Q10 (or ubiquinone) is a coenzyme present in the mitochondrial complexes involved in the oxidative phosphorylation lead to the production of ATP (Mitchell et al, 1976; Mitchell et al, 1990). The other fundamental property of the coenzyme Q10 is being an antioxidant, neutralizing free radicals (Beyer et al 1990, Villalba et al 1997).

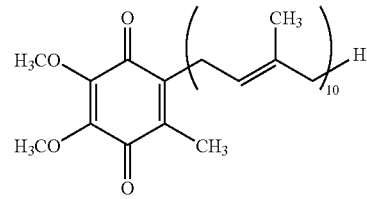

Coenzyme Q10 is a benzoquinone derivative flanked by a long lateral isoprene chain consisting more often of ten isoprenoid units (hence the name Coenzyme Q10). As this coenzyme is not water soluble, it is only found in lipid membranes such as the internal membrane of the mitochondria, where it can freely be released from the phospholipid membranes.

Coenzyme Q10 can exist in three states of oxidation: a reduced form (CoQH2 or UQH2), an oxidized form (CoQ10), and an intermediary form the radical ubisemiquinone (Q).

Coenzyme Q10 is present in the skin where it stimulates natural cell functions and acts to defend against external aggressions.

The biosynthesis of coenzyme Q10 is done by starting with the tyrosine for the quinone kernel, and starting with farnesyl pyrophosphate for the lateral chain. The enzyme responsible for this last reaction, which is an essential stage in the biosynthesis of the coenzyme Q10, is transprenyl transferase (or polyprenyl transferase).

The search for compositions able to stimulate the synthesis of coenzyme Q10, the energy synthesis of ATP and/or to protect cells damage caused by free radicals is a concern of medical and cosmetic research. Solutions has therefore been proposed to use peptide substances having antioxidant properties (WO2005097060, JP2006131626), but any cosmetic or pharmaceutical composition comprising the peptides or polypeptides of the present invention has yet to be described.

The inventors have shown a therapeutic activity, and more particularly dermatological and cosmetic activity, special peptides, described in the present invention. It has particularly been demonstrated that these peptides, when applied to the skin, have a strong protective activity with respect to the oxidative damage suffered by the skin and favoring to a significant degree the synthesis of ATP, and the synthesis or the activity of the enzyme transprenyl transferase and the coenzyme Q10. This new active principle, capable of increasing cell energy and protecting the skin from oxidative damage, thus makes it possible to open up new therapeutic and cosmetic perspectives.

"Active principle capable of increasing cell energy and protecting the skin from oxidative damages" means all substances capable of increasing the synthesis of intracellular ATP and to provide protective properties in the cells or tissues subject to physical-chemical or environmental oxidant stress.

Thus, the first purpose of the invention is a cosmetic or pharmaceutical composition, and particularly dermatological, comprising, in a physiologically adapted medium, as active principle, peptides capable of increasing cell energy and protecting the skin from oxidative damage, alone or in association with at least one other active principle.

The term "peptide" indicates a chain of two or more amino acids linked by peptide bonds or by modified peptide bonds. "Peptide" means the natural or synthetic peptide according to the invention as described above or at least one of its fragments, which are obtained by proteolysis or synthetically, or also all natural or synthetic peptides in which the sequence is totally or partially comprised by the sequence of the peptide according to the invention.

Preferably, according to this invention, the active principle according to the invention or its biologically active derivatives is composition of at least one peptide whose number of amino acids is between 5 and 13.

The expression "biologically active" means "that which possesses an in vivo or in vitro activity characteristic of the activity of the active principle according to the invention."

According to a particular embodiment of the invention, the peptide possesses a sequence that corresponds to the general formula (I)

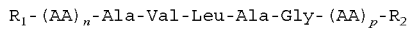

$$R_1\text{-}(AA)_n\text{-}Ala\text{-}Val\text{-}Leu\text{-}Ala\text{-}Gly\text{-}(AA)_p\text{-}R_2$$

In which

AA represents any amino acid, or one of its derivatives, and n and p are whole numbers between 0 and 4.

$R_1$ represents the primary amino function of the amino acid N-terminal, free or substituted by a protector group which can be selected from an acetyl group, a benzyl group, a tosyl group or a benzyloxycarbonyl group.

$R_2$ represents the hydroxyl function of the carboxyl acid of C-terminal amino acid, free or replaced by a protector group which can be selected from an alkyl chain from C1 to $C_{20}$, or a $NH_2$, NHY or NYY group with Y representing an alkyl chain from C1 to $C_4$.

According to a particularly preferred embodiment of the invention, the biologically active peptide is the sequence SEQ ID no 1 or the sequence SEQ ID no 2

```
(SEQ ID n°1)  Ala-Val-Leu-Ala-Gly-Asp-NH2

(SEQ ID n°2)  Ala-Val-Leu-Ala-Gly-Asp
```

The biologically active peptide can be the sequence SEQ ID NO: 3 or the sequence SEQ ID NO: 4.

(SEQ ID NO: 3) Ala-Val-Leu-Ala-Gly (SEQ ID NO: 4) Ala-Val-Leu-Ala-Gly-NH2

The invention also concerns homologous forms of these sequences. The term "homologous" designates, according to the invention, all peptide sequences at least 50% identical, or preferably at least 80%, and also more preferably at least 90% identical to the referenced peptide sequence, selected between the sequence SEQ ID no 1 and the sequence SEQ ID no 2. "at least X % identical Peptide sequence" designates a percent of identity between the residues of amino acids of the two sequences to be compared, obtained after the optimal alignment of the two sequences. The optimal alignment is obtained using algorithms of local homologous such as those used by the BLAST P or T BLAST N software available on the NCBI site.

The term "homologous" can also indicate a peptide which differs from the sequence of a peptide from the sequence SEQ ID no 1 or SEQ ID no 2 by the substitution of chemically equivalent amino acids, that it, by the replacement of one residue by another having the same characteristics. Thus, the classical substitutions are between Ala, Val, Leu and Ile; between Ser and Thr; between the acid residues Asp and Glu; between Asn and Gln; and between the basic residues Lys and Arg; or between the aromatic residues Phe and Tyr.

In the invention, the term "amino acid" refers to all natural or non-natural organic acids having the formula:

—NHR—CR—C(O)—O— where each —R is independently chosen between one hydrogen and one alkyl group having between 1 and 12 carbon atoms. Preferably, at least one —R group of each amino acid is a hydrogen. The term "alkyl" means a carbon chain that can be linear or branched, substituted (mono- or poly-) or non-substituted; saturated, monosaturated (a double or triple bond in the chain) or polyunsaturated (two or more doubles bonds, two or more triples bonds, one or more double bonds and one or more triple bonds in the chain).

"Peptide" means the natural or synthetic peptide according to the invention as described above or at least one of its fragments, which is obtained by proteolysis or synthetically, or also all natural or synthetic peptides whose sequence is totally or partially constituted by the sequence of the peptide described above.

In order to improve resistance to degradation, it may be necessary to use a protected form of the peptide according to the invention. The form of protection must evidently be a biologically compatible form and must be compatible with use in the field of cosmetics or pharmacy.

Many forms of biologically compatible protection can be imagined. Thus, the invention concerns a composition as defined above, characterized by the fact that the general formula peptide (I) possesses at least one functional group protected by a protector group, this protector group being either an acylation or an acetylation of the amino-terminal end, or an amidation or an esterification of the carboxy terminal end, or the two. The amino-terminal end can be protected by an acetyl group, a benzyl group, a tosyl group or a benzyloxycarbonyl group. Preferably, one uses a protection based on the amidation of the hydroxyl function of carboxy terminal end by a NYY group with Y representing an alkyl chain from C1 to $C_4$, or an esterification by an alkyl group. It is also possible to protect the two ends of the peptide.

The peptide derivatives also concern the amino acids and the peptides linked by a pseudo-peptide bond. "Pseudo-peptide bond" means all types of bonds able to replace the "classical" peptide bonds.

In the field of amino acids, the geometry of the molecules is such that they can theoretically take the form of different optic isomers. There exists, en effect, a molecular conformation of amino acid (AA) as it turns to the right the polarization plan of the light (dextrorotatory conformation or D-aa), and a molecular conformation of amino acid (aa) as it turns to the left the light polarization plan (levorotatory conformation or L-aa). Nature only provides for natural amino acids and levorotatory conformation. Consequently, a natural origin peptide can only comprise amino acids of the type L-aa. However, chemical synthesis in the laboratory makes it possible to prepare amino acids having the two possible conformations. Starting with this base material, it is thus also possible during peptide synthesis to incorporate equally well amino acids in the form of dextrorotatory optical isomers or levorotatory. Thus, amino acids making up the peptide according to the invention can be under the configuration L- and D-; preferentially, the amino acids are under form L. The peptide according to the invention can then be under the form L-, D- or DL-.

The general formula peptide (I) according to the invention can be obtained either by classical chemical synthesis (en solid phase or in homogenous liquid phase), or by enzyme synthesis (Kullman et al., J. Biol. Chem. 1980, 225, 8234), starting with constituent amino acids or their derivatives.

The peptide according to the invention can also be obtained from fermentation of a strain of bacteria modified or unmodified, by genetic engineering, or also by the extraction of animal or vegetable protein, preferably of vegetable origin, following by controlled hydrolysis which frees peptide fragments corresponding totally or partially to the general formula peptides (I).

Many proteins found in plants are likely to contain these sequences within their structure. Controlled hydrolysis makes it possible to release these peptide fragments. It is possible, but not necessary to realize the invention, to extract both the proteins concerned initially and then to hydrolyze them, and to do the hydrolysis initially on a raw extract and then to purify the peptide fragments. It is also possible to use certain hydrolyzed extracts without purifying the peptide fragments corresponding to the general formula peptides (I) according to the invention, but insuring the presence of said fragments by the appropriate analytical means.

Other simpler or more complex procedures can be envisioned by the person skilled in the art familiar with the synthesis, extraction and purification of proteins and peptides. Thus, the peptide according to the invention can be of natural or synthetic origin. Preferably according to the invention, the peptide is obtained by chemical synthesis. According to the invention, the active principle can be a mixture of peptide derivatives and/or made up of amino acid derivatives.

According to an advantageous embodiment of the invention, the active principle according to the invention is made soluble beforehand in one or more solvents classically used by the person skilled in the art, such as water, glycerol, ethanol, propylene glycol, butylene glycol, dipropylene glycol, ethoxylated or propoxylated diglycols, cyclic polyols, Vaseline, a vegetable oil or any mixture of these solvents.

According to still another advantageous embodiment of the invention, the active principle according to the invention is beforehand made soluble in a cosmetic or pharmaceutical vector such as liposomes or adsorbed on organic powder polymers, mineral supports such as talcs and bentonites, and more generally made soluble in, or fixed on, all cosmetically or pharmaceutically acceptable vectors.

It is well understood that the active principle according to the invention can be used alone or in association with at least one other active principle, in a cosmetic composition or for the preparation of a pharmaceutical and/or dermatological composition.

The compositions according to the invention can be applied by all appropriate paths, particularly orally, parenteral or topical external, and their formulation will be adapted by the person skilled in the art, in particular for cosmetic or dermatological compositions. Advantageously, the compositions according to the invention take a form adapted to topical application. The compositions must then contain a cosmetically and/or dermatologically acceptable medium, that it, compatible with the skin and the skin appendages, and cover all cosmetic or dermatological forms. These compositions can particularly be in the form of creams, oil-in-water emulsions, or water-in-oil or multiple emulsions, solutions, suspensions, gels, milks, lotions, sticks or also powders, adapted to application to the skin, the lips and/or the skin appendages.

These compositions comprise the excipients necessary for their formulation, such as solvents, thickeners, thinners, surfactants, anti-oxidants, dyes, preservatives, perfumes.

To be sure, the person skilled in the art will make sure to select possible complementary compositions, active or non-active, and/or their quantity, in such a way that the advantageous properties of the mixture are not, or not significantly, altered by the planned addition.

The composition utilizable according to the invention can in particular consist of a hair care composition, and particularly a shampoo, an after-shampoo, a waving lotion, a medicated lotion, a cream or a hair gel, a restructuring lotion for hair, a mask, etc. The cosmetic composition according to the invention can be used particularly in treatments implementing an application which is followed or not followed by rinsing, or also in the form of shampooing.

It can also take the form of a tincture or mascara to be applied to the brush or to the comb, in particular on the lashes, eyebrows or hair.

Advantageously, the utilizable compositions also contain at least one other active agent promoting the action of the peptides according to the invention. Thus, the composition can associate, to the active principle according to the invention, active agents having an antioxidant action, or also stimulating the synthesis of dermal macromolecules, or also stimulating energy metabolism. For example, as active agents having an antioxidant action, one can cite vitamin C, vitamin E, or polyphenol plant extracts.

One can also cite, as active agents stimulating the syntheses of dermal macromolecules (laminine, fibronectine, collagen), for example the collagen peptide marketed under the name "Collaxyl®" by the Vincience company.

Finally, as active agents stimulating energy metabolism, one can cite the active principle marketed under the name "GP4G®" by the Vincience company.

According to another aspect, the composition according to the invention can be a sun composition, that is, a composition helping to protect against sun rays. Thus, it can be advantageously added, to the composition according to the invention, active principles used for sun protection such as, for example, sun blocks.

It is quite evident that the invention is directed to mammals in general, and more particularly to human beings.

The effective quantity of the active principle corresponds to the peptide quantity according to the invention necessary to obtain the desired result, that is: increase the synthesis of ATP, protect the skin from oxidative damage and more generally, protect the skin from external aggressions and prevent or treat aging skin.

According to an advantageous embodiment of the invention, the general formula active principle (I) is present in the composition according to the invention in a concentration between approximately 0.0005 and 500 ppm (parts per million), and preferably at a concentration between approximately 0.01 and 5 ppm compared to the total weight of the final composition.

These compositions can particularly be present in the form of an aqueous solution, hydroalcoholic or oily; of an oil-in-water emulsion, water-in-oil or multiple emulsions; they can also take the form of creams, suspensions, or also powders, adapted to an application on the skin, the mucosa, the lips and/or the skin appendages. These compositions can be more or less liquid and have the appearance of a cream, a lotion, a milk, a serum, a pomade, a gel, a paste or a mousse. They can also take solid form, such as a stick or be applied to the skin under aerosol form. They can be used as a care product and/or as a skin makeup product.

These compositions comprise, in addition, all additives commonly used in the considered field of application as well as the additives necessary for their formulation, such as solvents, thickeners, thinners, antioxidants, dyes, sunblocks, self-tanning [principles], pigments, charges, preservatives, perfumes, air fresheners, cosmetic or pharmaceutical active [principles], essential oils, vitamins, essential surfactant fatty acids, polymers leaving a protective film, etc.

In any case, the person skilled in the art will make sure to that these additives and their proportions are selected in such a way as not to harm the advantageous properties sought in the composition according to the invention. These additives can, for example, correspond to from 0.01 to 20% of the total weight of the composition. When the composition according to the invention is an emulsion, the fat phase can represent from 5 to 80% by weight and preferably 5 to 50% by weight compared to the total weight of the composition. The emulsifiers and co-emulsifiers used in the composition will be selected from those classically used in the field in question. For example, they can be used in a proportion of between 0.3 to 30% by weight, compared to the total weight of the composition.

Due to these special activities, the active principle according to the invention can be used advantageously in a cosmetic composition or for the preparation of a pharmaceutical composition.

In particular, the active principle according to the invention can be used advantageously in a cosmetic composition to increase the synthesis of intracellular ATP of skin cells.

The active principle according to the invention can also be used advantageously in a cosmetic composition to increase the activity or the synthesis of the enzyme transprenyl transferase and/or the coenzyme Q10 in skin cells.

An essential aspect of the invention is the use of the invention active principle, in a cosmetic composition to protect the skin and the skin appendages from oxidative damage. Said active principle is advantageously used as antioxidant active principle, and/or as anti-radical active principle, and/or as active anti-glycation principle. Anti-radical active principle means all compositions capable of trapping free radicals before the final stages of degradation of the biologics making up the skin, in that case we refer to antioxidant compositions. Active anti-glycation principle means any/all composition capable of limiting cell damage caused by glycation or glycoxidation reactions. Thus, the active principle according to the invention will make it possible to combat esthetic damage to the skin and/or hair caused by free radicals.

Also, the active agent can be used advantageously in a cosmetic composition to protect the skin and the skin appendages against all types of external aggressions. The expression "external aggression" means aggressions that can be produced by the environment. For example, one can cite aggressions such as pollution, UV rays, or also products creating irritation such as surfactants, preservatives or perfumes. Pollution also means/includes "external" pollution, due for example to diesel particles, ozone or heavy metals, that "internal" pollution that can be due particularly to emissions of paint, glue, or wallpaper (such as astoluene, styrene, xylene or benzaldehyde), or also cigarette smoking.

Another aspect of the invention is the use of said active principle in a cosmetic composition or for the preparation of a pharmaceutical composition, as active photo-protector principle and, more particularly, as active photo-protector principle known as "secondary." In fact, a distinction is made between primary active photo-protectors principles and secondary active photo-protectors principles. Primary active photo-protectors principles are substances which exert a physical power: they are able to absorb UV rays and to return them in the form of heat in order to protect the skin. Secondary active photo-protectors principles are substances which instead have a biological effect; these are, for example, active antioxidant-type principles which interrupt the chains of photochemical reactions which are triggered when UV rays penetrate the skin.

In another essential aspect of the invention, the active principle can be used advantageously in a cosmetic composition to fight in a preventive and/or curative fashion against the signs of skin aging, and more specifically, to combat and/or prevent light induced aging (photo-aging). Skin aging signs means all modifications of the exterior appearance of the skin and the skin appendages due to aging such as, for example, lines and wrinkles, wilted skin, flabby skin, drawn skin, lack of elasticity and/or skin tone, dull skin or skin pigment spots, hair discoloration or spots on nails, but also all internal changes of the skin which are not systematically translated by a changed exterior appearance such as, for example, all oxidative damage of the skin resulting from exposure to ultraviolet rays (UV). The active principle according to the invention, or the composition containing it, will make it possible to fight, in particular, against loss of skin elasticity and firmness.

The purpose of the invention is also to be used in a cosmetic composition of an effective quantity of active principle as described above, to prevent the damage caused to the skin by exposure to the sun or exposure to ionizing rays during radiotherapy.

The purpose of the invention is also the use in a cosmetic composition, of an effective quantity of active principle as described above, to stimulate and/or protect mitochondria, in particular on the areas of the body exposed to UV rays.

The invention also consists of a pharmaceutical composition characterized in that the active principle according to the invention is formulated to alleviate a pathology linked to oxidation processes, or also certain aging pathologies.

The invention also consists of a cosmetic treatment procedure aimed at protecting the skin and the skin appendages from external aggressions and to fight skin aging characterized by the application to the skin or the skin appendages to be treated a composition containing an effective quantity of active principle according to the invention.

Special embodiments of this cosmetic treatment procedure are also shown in the description above. Other advantages and characteristics of the invention will be more apparent by reading examples provided for non-limiting illustrative purposes.

EXAMPLE 1

Assessment of the Activator Effect of the Peptide SEQ ID No 2 on the Synthesis of Intracellular ATP The goal of this study is to determine the influence of the peptide SEQ ID no 2 on the synthesis of ATP.

Protocol

This study was conducted using an "ATP Bioluminescence Assay Kit HS II" Kit (Roche Applied Science):

The dermal fibroblasts are treated with a 1% solution, a solution a 50 ppm, containing the peptide SEQ ID no 2, representative of the family of peptides according to the invention, for a period lasting from 1 to 3 hours. At the end of the incubation period, the wells are emptied of their medium and rinsed with 2 ml of cold PBS before adding 250 µl of a lysis buffer supplied by the kit. The cells of each well are then scrapped, then collected in 14 ml tubes. Each well is rinsed with 2×500 µl of cold PBS and everything is against collected the respective tubes. Beginning with these samples, a $1/12000^{th}$ dilution is done in cold PBS before each reading. The dosage of ATP is done on these samples: 50 µL of this dilution is placed in a luma basin and 50 µl of luminol are added. After 10 seconds, the luminescence read is triggered. The values are standardized with respect to the quantity of proteins for each sample. The measures are done using an apparatus: the Biocounter M2010A LUMAC®/3M.

Results

The measurements of ATP show that there is a 17% increase in the quantity of intracellular ATP after 1 hour and 67% after 3 hours of culture in cells treated by the peptide SEQ ID No 2, compared to the untreated cells.

Conclusion

The peptide SEQ ID no 2 greatly activates the synthesis of intracellular ATP in skin cells.

EXAMPLE 2

Assessment of the Protector Effect of the Peptide SEQ ID No 1 with Respect to Oxidative Damage The goal of this study is to determine the protector effect of the peptide SEQ ID no 1 with respect to dermal fibroblasts subjected to oxidative stress caused by UV rays or hydrogen peroxide ($H_2O_2$). To evaluate the oxidative damage suffered by the cells, measurements of the carbonylation of the proteins was done.

The carbonylation of proteins is the result of the oxidative splitting of proteins or oxidation of the arginine residues, lysine, proline or threonine. The dosage of the carbonylation of proteins is done using an EIA (Enzyme Immuno Assay) technique.

Protocol

Fibroblasts in culture were placed in the presence of the peptide SEQ ID no 1 in a 1% solution, at 50 ppm, 72 hours before, during, and also 24 hours after the oxidative stress (UVB irradiation of 50 mJ/cm$^2$ or treatment par 2 mM of $H_2O_2$). untreated controls not subjected to oxidative stress are done.

The degree of carbonylation consists in the use of DNP (dinitrophenyl) which has the property to se fixer specifically on these carbonyl groups of the proteins. The fixed DNP is then assayed using an ELISA method, thanks to an anti-DNP antibody linked to peroxydase. A range of BSA (bovine albumin serum) oxidized (with a known concentration of carbonyl groups) is used for calibration.

Results

The results achieved show a 30% reduction in the carbonylation of proteins when the cells are treated with the peptide SEQ ID no 1 according to the invention, compared to the untreated cells.

More particularly, one observes a 20% decrease in carbonylation when the cells treated with the peptide SEQ ID no 1 are subjected to irradiation by UVB or to an oxidative stress by $H_2O_2$, compared to the irradiated or stressed cells not treated with the active principle.

Conclusion

The peptide SEQ ID no 1 effectively protects the skin cells against oxidative damage caused by UVB rays or hydrogen peroxide.

EXAMPLE 3

Assessment of the Protector Effect of the Peptide SEQ ID No 1 with Respect to Stress Induced by Glycation The goal of this study is to determine the protective effective of the peptide SEQ ID no 1, with respect to ex vivo epidermal culture subjected to stress by a glycation agent.

Protocol

Biopsies of human skin are maintained in ex vivo culture, treated with a 1% solution, a mother solution of 50 ppm of peptide SEQ ID no 1, 24 hours before, and also 24 hours after the introduction of a glycation agent (methyl glyoxal at 5 or 10 mM). Histology hematoxyline-eosine (H&E) staining makes it possible to evaluate the quality of skin structures.

Results

The evaluation of the skin structures shows a net resistance to cellular stress induced by glycation of biopsies of skin treated with the peptide SEQ ID no 1.

Conclusion

The peptide SEQ ID no 1 protects the skin from stress induced by glycation.

EXAMPLE 4

Preparation of Compositions

1—Sun Protection Cream:

| Trade names | INCI Names | % W/W |
|---|---|---|
| PHASE A | | |
| Demineralized water | Aqua (Water) | qsp |
| Pemulen TR1 | Acrylates/C10-30 Alkyl Acrylate Crosspolymer | 0.40 |
| Glycerin | Glycerin | 3.00 |
| Nipastat Sodium | Sodium Methylparaben (and) Sodium Ethylparaben (and) Sodium Butyl paraben (and) Sodium Propylparaben (and) Sodium Isobutylparaben | 0.15 |
| PHASE B | | |
| Parsol MCX | Ethylhexyl Methoxycinnamate | 7.50 |
| Eusolex 4360 | Benzophenone-3 | 3.00 |
| Parsol 1789 | Butyl Methoxydibenzoylmethane | 2.00 |
| Myritol 318 | Caprylic/Capric Triglyceride | 4.00 |
| Emulgade SEV | Hydrogenated Palm Glycerides (and) Ceteareth-20 (and) Ceteareth-12 (and) Cetearyl Alcohol | 5.00 |
| Propylparaben | Propylparaben | 0.15 |
| Nacol 16-98 | Cetyl Alcohol | 1.00 |
| PHASE C | | |
| TEA | Triethanolamine | 0.20 |
| PHASE D | | |
| Peptide SEQ ID n° 1 | | 3 ppm |
| Perfume | Perfume (Fragrance) | qsp |
| Dye | | qsp |

The components of phase A and phase B are heated separately to between 70° C. and 75° C. Phase B is emulsified in phase A under agitation. Phase C is added, to 45° C., increasing the agitation. Phase D is then added when the temperature is below 40° C. The cooling is continued to 25° C. under lively agitation.

2—After-Sun Milk:

| Trade names | INCI Names | % w/w |
|---|---|---|
| PHASE A | | |
| Montanov L | C14-22 Alcohols (and) C12-20 Alkyl Glucoside | 3.00 |
| Waglinol 2559 | Cetearyl Isononanoate | 4.00 |
| Tegosoft TN | C12-15 Alkyl Benzoate | 3.00 |
| Apricot kernel oil | *Prunus Armeniaca* (Apricot) Kernel Oil | 2.00 |
| Avocado oil | *Persea Gratissima* (Avocado) Oil | 1.00 |
| Abil 350 | Dimethicone | 1.00 |
| PHASE B | | |
| Demineralized Water | Aqua (Water) | qsp |
| PHASE C | | |
| Simulgel EG | Sodium Acrylate/Acryloyldimethyl Taurate Copolymer (and) Isohexadecane (and) Polysorbate 80 Copolymer (and) Polysorbate 80 | 0.4 |

-continued

| Trade names | INCI Names | % w/w |
|---|---|---|
| PHASE D | | |
| Phenonip | Phenoxyethanol (and) Methylparaben (and) Ethylparaben (and) Butylparaben (and) Propylparaben (and) Isobutylparaben Ethylparaben and Propylparaben and Buthylparaben | 0.30 |
| Germall 115 | Imidazolidinyl Urea | 0.20 |
| PHASE E | | |
| Peptide SEQ ID n° 2 | | 0.1 ppm |

Prepare phase A under agitation. Progressively incorporate the xanthan gum, under deflocculating agitation. Phases C and D will be incorporated once the gel is ended. Phase E, prepared beforehand until the DHA is fully dissolved, will then be added. Adjust the pH if necessary to 4-4.5. Dye and perfume.

3—Anti-Aging Cream:

| Trade names | INCI Names | % w/w |
|---|---|---|
| Phase A | | |
| Montanov 68 | Cetearyl Alcohol (and) Cetearyl Glucoside | 6.00 |
| Squalane | Squalane | 3.00 |
| Cetiol SB 45 | *Butyrospermum Parkii* (Shea Butter) | 2.00 |
| Waglinol 250 | Cetearyl Ethylhexanoate | 3.00 |
| Amerchol L-101 | Mineral Oil (and) Lanolin Alcohol | 2.00 |
| Abil 350 | Dimethicone | 1.50 |
| BHT | BHT | 0.01 |
| Phase B | | |
| Avocado oil | *Persea Gratissima* (Avocado) Oil | 1.25 |
| Phenonip | Phenoxyethanol (and) Methylparaben (and) Ethylparaben (and) Butylparaben (and) Propylparaben (and) Isobutylparaben | 0.75 |
| Phase C | | |
| Demineralized water | Aqua (Water) | qsp |
| Butylene Glycol | Butylene Glycol | 2.00 |
| Glucam E10 | Methyl Gluceth-10 | 1.00 |
| Allantoin | Allantoin | 0.15 |
| Carbopol Ultrez 10 | Carbomer | 0.20 |
| Phase D | | |
| TEA | Triethanolamine | 0.18 |
| Phase E | | |
| Peptide SEQ ID n°1 | | 0.5 ppm |
| GP4G | Water (and) *Artemia* Extract | 1.50 |
| Collaxyl | Water (and) Butylene Glycol (and) Hexapeptide-9 | 3.00 |
| Phase F | | |
| Perfume | Perfume (Fragrance) | qsp |
| Dye | | qsp |

Prepare and blend phase A at 65-70° C. Heat phase C at 65-70° C. Phase B is added at phase A just before emulsifying A in B. A approximately 45° C., the carbomer is neutralized by addition of phase D. Phase E is then added under light agitation and cooling is continued to 25° C. Phase F is then added if desired.

4—Day Protector Cream:

| Brand names | INCI Name | % w/w |
|---|---|---|
| Phase A | | |
| Emulium Delta | Cetyl alcohol (and) Glyceryl Stearate (and) PEG-75 Stearate (and) Ceteth-20 (and) Steareth-20 | 4.00 |
| Lanette O | Cetearyl Alcohol | 1.50 |
| D C 200 Fluid/100cs | Dimethicone | 1.00 |
| DUB 810C | Coco Caprylate/Caprate | 1.00 |
| DPPG | Propylene Glycol Dipelargonate | 3.00 |
| DUB DPHCC | Dipentaerythrityl Hexacaprylate/Hexacaprate | 1.50 |
| Cegesoft PS6 | Vegetable Oil | 1.00 |
| Vitamin E | Tocopherol | 0.30 |
| Phenonip | Phenoxyethanol (and) Methylparaben (and) Ethylparaben (and) Butylparaben (and) Propylparaben (and) Isobutylparaben | 0.70 |
| Phase B | | |
| Demineralized water | Aqua | qsp 100 |
| Glycerin | Glycerin | 2.00 |
| Carbopol EDT 2020 | Acrylates/C10-30 Alkyl Acrylate Crosspolymer | 0.15 |
| Keltrol BT | Xanthan Gum | 0.30 |
| Phase C | | |
| Sodium Hydroxide (10% solution) | Sodium Hydroxide | 0.30 |
| Phase D | | |
| Demineralized water | Aqua | 5.00 |
| Stay-C 50 | Sodium Ascorbyl Phosphate | 0.50 |
| Phase E | | |
| Butylene Glycol | Butylene Glycol | 2.00 |
| Dekaben CP | Chlorphenesin | 0.20 |
| Phase F | | |
| GP4G | Water (and) *Artemia* Extract | 1.00 |
| Peptide SEQ ID n°2 | | 5 ppm |

Prepare phase A and heat to 75° C. under agitation. Prepare phase B dispersing the carbopol, then the xanthan gum under agitation. Let rest. Heat to 75° C.

At temperature, emulsify A in B under rotor-stator agitation. Neutralize with phase C under rapid agitation. After cooling to 40° C., add phase D, then phase E. Cooling is continued under light agitation and phase F added.

The invention claimed is:

1. A composition comprising:
an active principle in a physiologically acceptable medium, said active principle comprising a peptide wherein,
said peptide comprises from 5 to 6 residues of amino acids, and
said peptide has a sequence according to formula (I):

$R_1$-Ala- Val- Leu- Ala- Gly-$(AA)_p$-$R_2$ in which
AA represents any amino acid, and p is 0 or 1,
$R_1$ represents the primary amino function of the amino acid N-terminal, free or substituted by a protector group selected from the group consisting of an acetyl group, a benzyl group, a tosyl group and a benzyloxycarbonyl group, and
$R_2$ represents the hydroxyl function of carboxyl acid of the amino acid C-terminal, free or substituted by a protector group selected from (i) an alkyl chain from $C_1$ to $C_{20}$, or (ii) an $NH_2$ group, an NHY group or an NYY group with Y representing an alkyl chain from $C_1$ to $C_4$.

2. The composition according to claim 1, wherein said peptide consists of the sequence Ala-Val -Leu-Ala-Gly-Asp-$NH_2$ (SEQ ID NO: 1).

3. The composition according to claim 1, wherein said peptide consists of the sequence Ala-Val -Leu-Ala-Gly-Asp (SEQ ID NO: 2).

4. The composition according to claim 1, wherein said peptide possesses at least one functional group protected by a protector group, said protector group being either at least one of (i) an acylation or an acetylation of the amino-terminal end and (ii) an amidation or an esterification of the carboxyterminal end.

5. The composition according to claim 1, wherein said active principle is present in the composition in a concentration between 0.0005 and 500 ppm approximately compared to the total weight of the composition.

6. The composition according to claim 5, wherein said active principle is present in the composition in a concentration between 0.01 and 5 ppm compared to the total weight of the composition.

7. The composition according to claim 1, wherein said active principle made soluble in one or more solvents cosmetically or pharmaceutically acceptable selected from the group consisting of water, glycerol, ethanol, propylene glycol, butylene glycol, dipropylene glycol, ethoxyl or propoxyl diglycols, cyclic polyols, petroleum jelly, a vegetable oil and mixtures thereof.

8. The composition according to claim 1, wherein the composition is in a topical application form.

9. The composition according to claim 1, further comprising at least one other active agent promoting the action of said active principle.

10. The composition according to claim 9, wherein said other active agent is selected from the group consisting of active agents having an antioxidant action, active agents stimulating the synthesis of macromolecules, and active agents stimulating energy metabolism.

11. A method of preparing a cosmetic composition or a pharmaceutical composition according to claim 1, comprising adding an effective amount of active principle to a physiologically acceptable medium.

12. A method of increasing the synthesis of intracellular ATP in the cells of the skin, comprising administering to a subject in need thereof a cosmetic composition according to claim 1 having an effective amount of active principle.

13. A method of increasing the activity or the synthesis of the enzyme transprenyl transferase and/or of the coenzyme Q10 in the cells of the skin, comprising administering to a subject in need thereof a cosmetic composition according to claim 1 having an effective amount of active principle.

14. A method of protecting the skin and the skin appendages against all types of external aggressions, comprising administering to a subject in need thereof a cosmetic composition according to claim 1 having an effective amount of active principle.

15. A method of preventing or treating damage caused to the skin and the skin appendages by UV rays, comprising administering to a subject in need thereof a cosmetic composition according to claim 1 having an effective amount of active principle.

16. A method of protecting the skin and the skin appendages from oxidative damage, comprising administering to a subject in need thereof a cosmetic composition according to claim 1 having an effective amount of active principle.

17. A method of preventing or treating the skin signs of aging and/or photoaging, comprising administering to a subject in need thereof a cosmetic composition according to claim 1 having an effective amount of active principle.

18. A method for preparing a pharmaceutical composition according to claim 1 for preventing or combating pathologies linked to the oxidation processes, comprising adding an effective amount of active principle to a physiologically acceptable medium.

19. A method of treating the skin and the skin appendages from external aggressions and to combat skin aging, comprising topically applying to the skin or the skin appendages of a subject in need thereof a cosmetic composition according to claim 1.

20. The composition according to claim 1, wherein said peptide consists of the sequence Ala-Val-Leu-Ala-Gly (SEQ ID NO: 3).

21. The composition according to claim 1, wherein said peptide consists of the sequence Ala-Val-Leu-Ala-Gly-$NH_2$ (SEQ ID NO: 4).

* * * * *